US00PP27889P3

(12) United States Plant Patent
Van Dijk

(10) Patent No.: US PP27,889 P3
(45) Date of Patent: Apr. 11, 2017

(54) ***ANTHURIUM* PLANT NAMED 'ANTHDUBAQ'**

(50) Latin Name: ***Anthurium andreanum* L.**
Varietal Denomination: ANTHDUBAQ

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 84 days.

(21) Appl. No.: 14/545,418

(22) Filed: May 1, 2015

(65) Prior Publication Data

US 2016/0324055 P1 Nov. 3, 2016

(51) Int. Cl.
*A01H 5/02* (2006.01)

(52) U.S. Cl.
USPC ..... Plt./368

(58) Field of Classification Search
USPC ..... Plt./368, 365, 369
See application file for complete search history.

(56) References Cited

PUBLICATIONS

Upov Pluto Plant Variety Database Sep. 2, 2016 for *Anthurium* 'Anthdubaq' retireved on Sep. 6, 2016, retrieved from the Internet at <http://www.upov.int/pluto/en/index.jsp> one page.*
EU Community Plant Variety Rights Application No. 2013/1864, Application n°A201300732, filed Jul. 5, 2013, 7 pages.
EU Community Plant Variety Office Official Gazette, May 2013, Oct. 15, 2013, cover page and pp. 29, 48.
*Anthurium* catalogue: Cut flower & pot plant 2015/2016, published May 2015, pp. 1, 39, 58.

* cited by examiner

*Primary Examiner* — June Hwu
(74) *Attorney, Agent, or Firm* — Jondle & Associates, P.C.

(57) ABSTRACT

A new and distinct variety of *Anthurium* plant named 'ANTHDUBAQ' particularly characterized by having a shiny, red-purple spathe, a purple spadix, a compact plant habit, a long-ovate leaf shape with a truncate base, and shiny, dark green foliage, is disclosed.

3 Drawing Sheets

Genus and species: *Anthurium andreanum* L.
Variety denomination: 'ANTHDUBAQ'.

BACKGROUND OF THE NEW PLANT

The present invention comprises a new and distinct variety of *Anthurium*, botanically known as *Anthurium andreanum* L., and hereinafter referred to by the variety name 'ANTHDUBAQ'. The new variety originated from a hybridization made in November 2006 in Bleiswijk, The Netherlands. The female parent is a purple *Anthurium* pot plant designated 'ANTHUCOEN' (U.S. Plant Pat. No. 22,630), and the male parent was a purple *Anthurium* plant designated '10441-04' (unpatented).

A single plant was selected in November 2008 and has been asexually reproduced repeatedly by meristem tissue culture in Bleiswijk, The Netherlands over a seven-year period. The present invention has been found to retain its distinctive characteristics through successive asexual propagations.

Plant Breeder's Rights for this variety have been applied for in the European Union on Jul. 5, 2013 and in Vietnam on Mar. 23, 2015. 'ANTHDUBAQ' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Shiny, red-purple spathe;
2) Purple spadix;
3) Compact plant habit;
4) Long-ovate leaf shape with a truncate base; and
5) Shiny, dark green foliage.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 27-week old plant grown in a greenhouse in Bleiswijk, The Netherlands in April 2015.

DESCRIPTION OF THE NEW VARIETY

Figure 1:
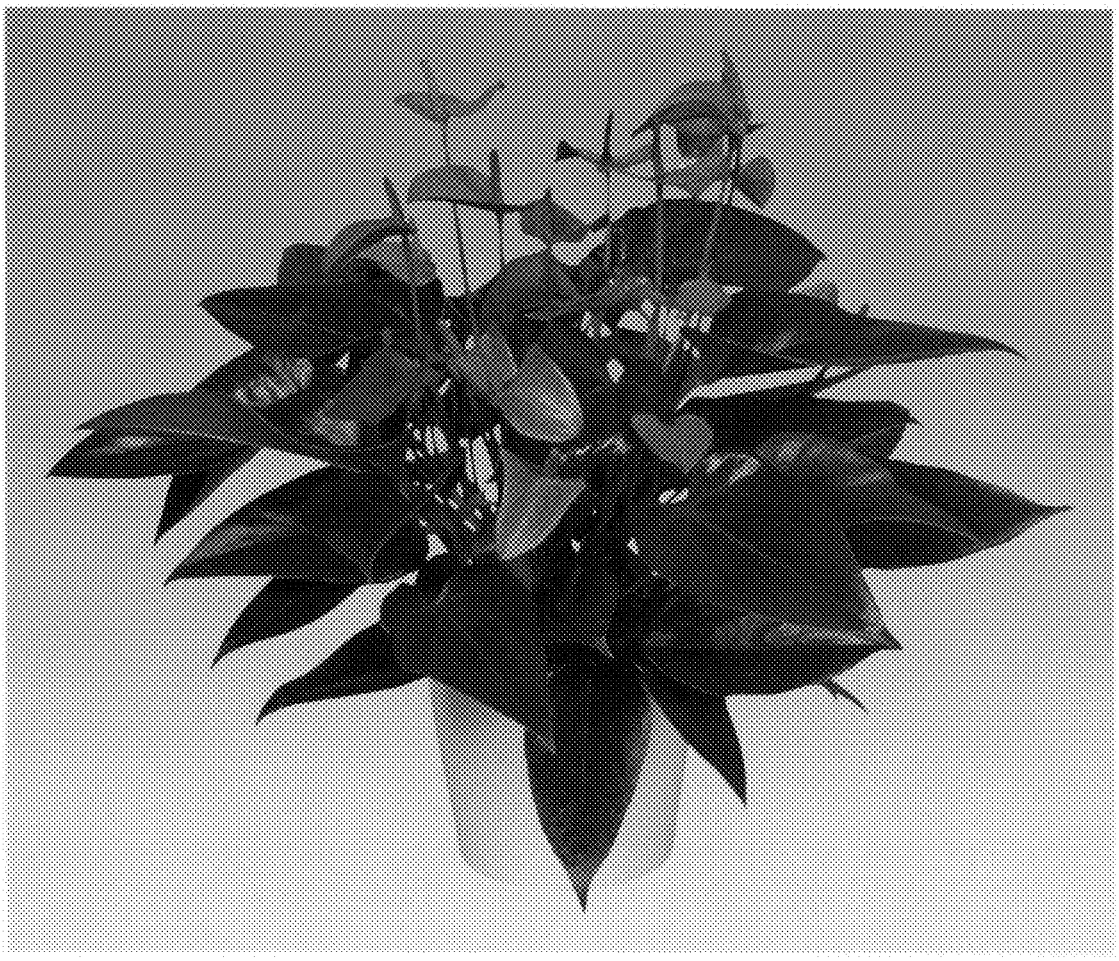
FIG. 1 shows the overall plant habit, including blooms, bud and foliage.
Figure 2:
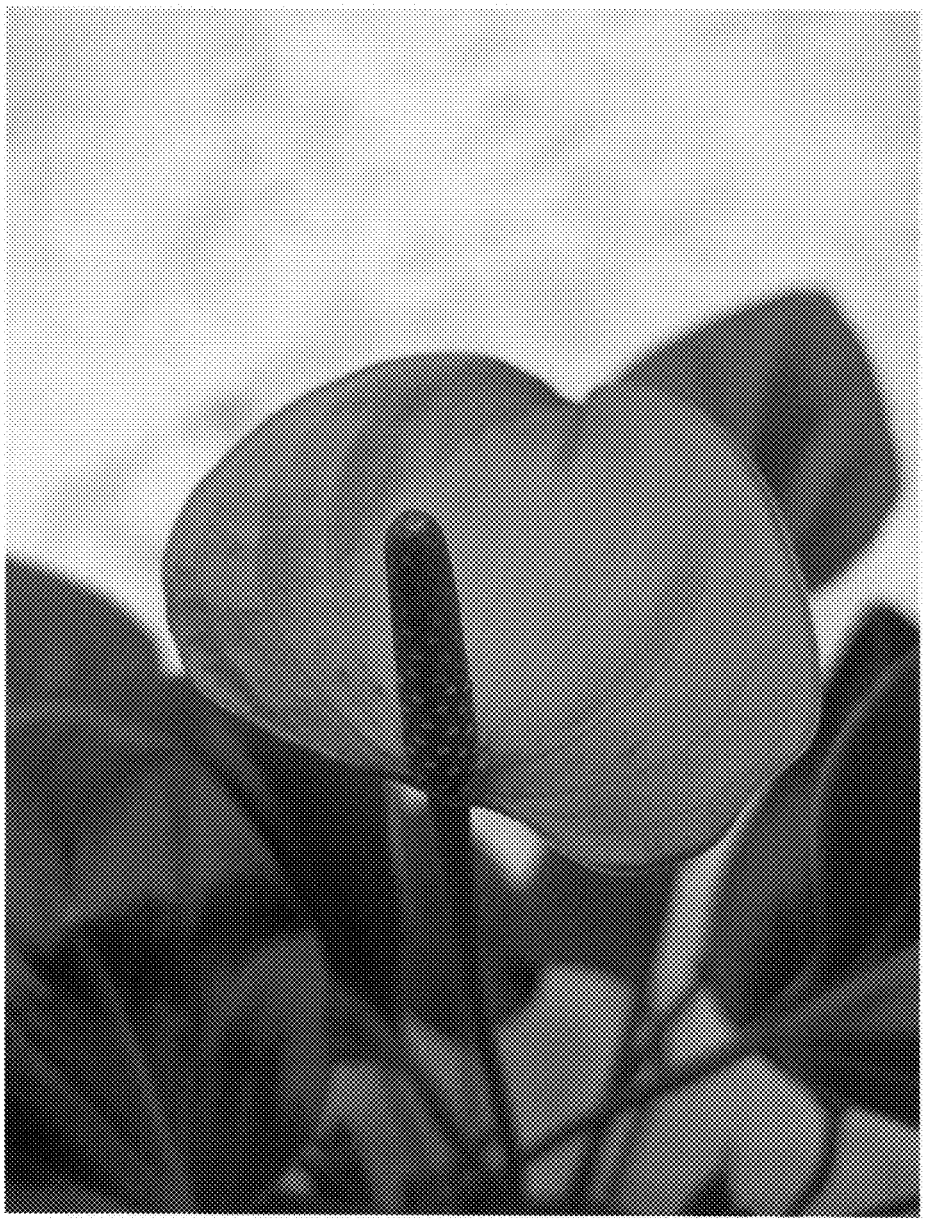
FIG. 2 shows a close-up of the mature spathe.
Figure 3:
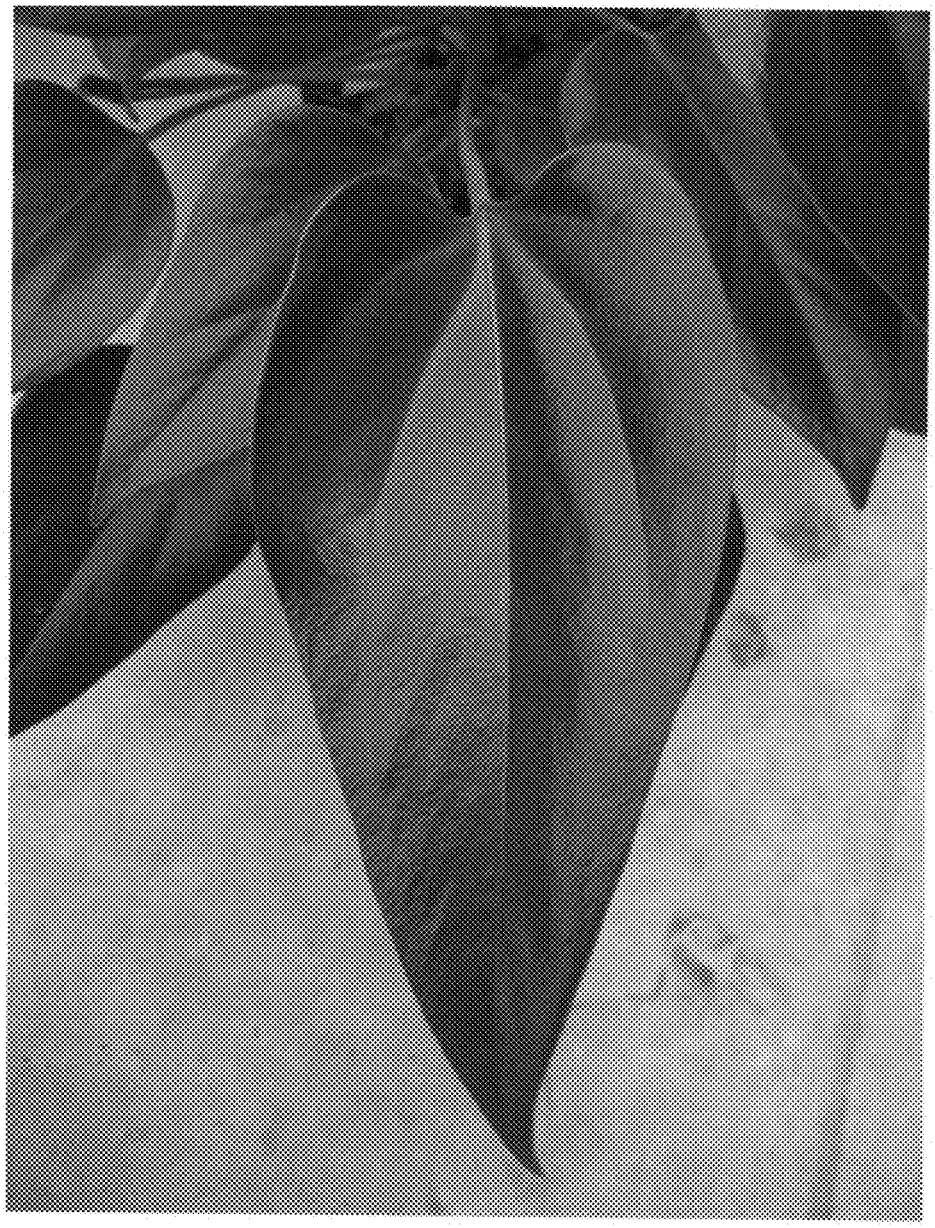
FIG. 3 shows the upper leaf blade surface.

The following detailed description sets forth the distinctive characteristics of 'ANTHDUBAQ'. The data which define these characteristics were collected from asexual reproductions carried out in Bleiswijk, The Netherlands. The plant history was taken on 27-week old plants which were planted from tissue culture in 12-centimeter pots and grown in a glass greenhouse between 19° C. and 24° C. Observations were made in April 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHDUBAQ'.

Parentage:

*Female parent*.—*Anthurium* plant 'ANTHUCOEN' (U.S. Plant Pat. No. 22,630).

*Male parent*.—*Anthurium* plant '10441-04' (unpatented).

Plant:

*Propagation*.—Tissue culture.

*Root description*.—Fleshy white-cream colored roots with small hairy lateral roots having yellow-colored root tips.

*Time to produce a finished flowering plant*.—25 to 30 weeks for a 12 cm pot.

*Growth habit*.—Herbaceous perennial.

*Height* (*measured from soil, including inflorescence*).—28.0 cm to 32.0 cm.

*Width* (*measured from leaf tips*).—42.0 cm to 52.0 cm.

Leaves:

*Immature leaves*.—Length: 10.0 cm to 14.0 cm. Width: 5.0 cm to 7.0 cm. Color: Upper surface: RHS 146A. Lower surface: RHS 146B. Texture (both upper and lower surfaces): Shiny.

*Mature leaves*.—Length (fully expanded): 10.0 cm to 16.0 cm. Width: 6.0 cm to 8.0 cm. Shape: Long-ovate. Apex: Acute. Base: Truncate. Leaf blade angle with the petiole: Between 120 degrees and 160 degrees. Leaf margin: Entire. Color: Upper surface: RHS 147A. Lower surface: RHS 146A. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144B. Lower surface: RHS 144B.

*Lobes*.—Arrangement: Leaf blade has no lobes extending past the petiole. Distance from petiole/leaf junction to highest point on lobes of mature leaf blades: 2.0 cm to 3.0 cm.

*Petiole*.—Cross-section: Round. Diameter: 0.15 cm to 0.25 cm. Length: 11.0 cm to 14.0 cm for a mature leaf size. Color: Mature leaf: RHS 144A. Immature leaf: RHS 144B. Cataphyll color surrounding the petiole: Outside: RHS 144C. Inside: RHS 145B.

*Geniculum*.—Length: 1.5 cm to 2.5 cm. Width: 0.2 cm to 0.3 cm. Color: RHS 144B.

Inflorescence:

*Arrangement*.—Single.

*Flowering habit* (*length of flowering season*).—Continuous.

*Number of inflorescences per plant*.—9 to 11.

*Fragrance*.—Absent.

*Longevity of inflorescence on plant*.—Over a year.

*Longevity of the flower as a cut flower*.—25 to 35 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 80 degrees and 110 degrees; the spathe stands on a wiry peduncle about 0 cm to 2.0 cm above the foliage.

*Shape*.—Cordate with very small lobes.

*Apex*.—Acuminate.

*Base*.—Cordate.

*Texture*.—Shiny and smooth.

*Margin*.—Entire.

*Blistering*.—Strong.

*Size*.—Height: 4.5 cm to 6.5 cm. Width: 4.5 cm to 6.5 cm.

*Color*.—Just fully open: Upper surface: RHS 61A. Lower surface: RHS 80C. Approximately 15 to 25 weeks after opening, veins in the spathe start greening to RHS 147A.

Peduncle:

*Shape*.—Erect.

*Cross-section*.—Round.

*Length*.—14.0 cm to 24.0 cm.

*Diameter*.—0.15 cm to 0.25 cm.

*Color*.—RHS 146A.

Flowering time:

*General*.—One small rooted untreated tissue culture plant of 2.0 cm tall will flower after 4 to 6 months, depending on the season, and 7 to 9 blossoms will appear. More blossoms appear after some additional weeks so that a full flowering and commercial plant will have 9 to 11 purple spathes. Smaller blossoms may occur on less mature plants.

Spadix:

*Size*.—Length: 1.5 cm to 3.5 cm (depending on flower size). Width (at apex): 0.35 cm to 0.45 cm. Width (at base): 0.5 cm to 0.6 cm.

*Shape*.—Columnar.

*Angle from spadix tip to peduncle*.—160-180 degrees (spadix is almost in one line with peduncle).

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 79C. Mature: RHS 77A. Ages to: RHS 177A.

Flowers:

*Quantity per spadix*.—180 to 200.

*Spadix flower arrangement*.—Bisexual, rounded in cross-section.

*Shape*.—Rounded.

*Size*.—Length: 0.05 cm to 0.1 cm. Diameter (maximum): 0.1 cm.

*Color*.—RHS 77A.

Reproductive organs:

*Stamens*.—Not visible.

*Pollen amount*.—Very few.

*Pollen color*.—RHS 156D.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed.

Disease and pest resistance: Not observed to date.

COMPARISON WITH PARENTAL AND COMMERCIAL VARIETIES

'ANTHDUBAQ' differs from the female parent plant 'ANTHUCOEN' (U.S. Plant Pat. No. 22,630) in that 'ANTHDUBAQ' has a deep red-purple spathe, whereas 'ANTHUCOEN' has a purple spathe.

'ANTHDUBAQ' differs from male parent plant '10441-04' (unpatented) in that 'ANTHDUBAQ' has a cordate shaped spathe with very small lobes, whereas '10441-04' has a long-ovate shaped spathe.

'ANTHDUBAQ' differs from commercial variety 'ANTHEMIEL' (unpatented) in that 'ANTHDUBAQ' has a purple spadix, whereas 'ANTHEMIEL' has a white spadix with yellow tip. Additionally, 'ANTHDUBAQ' has a truncate leaf base, whereas 'ANTHEMIEL' has a cordate leaf base.

'ANTHDUBAQ' differs from commercial variety 'ANTHCEQBOK' (unpatented) in that 'ANTHDUBAQ' has a red-purple spathe (RHS 61A), whereas 'ANTHCEQBOK' has a red/purple spathe (RHS 60A). Additionally, 'ANTHDUBAQ' has a truncate leaf base, whereas 'ANTHCEQBOK' has a cordate leaf base.

I claim:

1. A new and distinct variety of *Anthurium* plant named 'ANTHDUBAQ', substantially as illustrated and described herein.

* * * * *